United States Patent [19]
Baudino et al.

[11] Patent Number: 5,848,987
[45] Date of Patent: Dec. 15, 1998

[54] MICROTEXTURED CATHETER AND METHOD FOR PREVENTING CATHETER FLUID REFLUX

[75] Inventors: Michael D. Baudino, Coon Rapids; Mark T. Rise, Monticello; Maura G. Donovan, St. Paul, all of Minn.

[73] Assignee: Medtronic, Inc., Minneapolis, Minn.

[21] Appl. No.: 640,373

[22] Filed: Apr. 30, 1996

[51] Int. Cl.⁶ .................................. A61M 31/00
[52] U.S. Cl. .................. 604/54; 604/49; 604/93
[58] Field of Search ................. 604/49, 50, 51, 604/93, 174, 175, 264, 265, 266, 272; 623/1, 11, 12

[56] References Cited

U.S. PATENT DOCUMENTS

| | | | |
|---|---|---|---|
| 3,638,649 | 2/1972 | Ersek | 604/175 |
| 3,700,380 | 10/1972 | Kitrilakis | 623/12 |
| 4,798,585 | 1/1989 | Inoue et al. | 604/175 |
| 4,863,426 | 9/1989 | Ferragamo et al. | 604/93 |
| 5,122,114 | 6/1992 | Miller et al. | 604/49 |
| 5,190,529 | 3/1993 | McCrory et al. | 604/280 |
| 5,219,361 | 6/1993 | von Recum et al. | 623/11 |
| 5,289,831 | 3/1994 | Bosley | 623/12 |
| 5,308,338 | 5/1994 | Helfrich | 604/175 |
| 5,564,439 | 10/1996 | Picha | 604/175 |

FOREIGN PATENT DOCUMENTS

| | | | |
|---|---|---|---|
| 8801460 | 7/1980 | WIPO | 604/265 |

OTHER PUBLICATIONS

Triolo and Andrade, "Surface modification and evaluation of some commonly used catheter materials. I. Surface properties", Journal of Biomedical Materials Research, vol. 17, pp. 129–147(1983).

Triolo and Andrade, "Surface modification and characterization of some commonly used catheter materials. II. Friction characterization" JBMR, V. 17, 149–165, (1983).

von Recum, "New Aspects of Biocompatibility: Motion at the Interface", Clinical Implant Materials, Advances in Biomaterials, vol. 9, 1990.

Campbell and von Recum, "Microtopography and Soft Tissue Response", Journal of Investigative Surgery, vol. 2, pp. 51–74, 1989.

Bakey, Vitek and DeLong, "Thalamotomy for Tremor", Neurosurgical Operative Atlas, vol. 2, No. 4, pp. 299–312.

Meyle, Wolburg and von Recum, "Surface Micromorphology and Cellular Interactions", Journal of Biomaterials Applications, vol. 7, pp. 362–374, Apr. 1993.

*Primary Examiner*—John D. Yasko
*Assistant Examiner*—Jennifer R. Sadula
*Attorney, Agent, or Firm*—Curtis D. Kinghorn; Harold R. Patton

[57] ABSTRACT

A catheter having a microtextured exterior surface portion is employed to deliver fluids such as medicaments internally to the parenchyma of an organ or other internal living bodily tissue. The microtextured exterior surface portion promotes cellular tissue ingrowth into the textured surface, thereby creating an effective fluid seal in the bore formed in the tissue and inhibiting the body's rejection response to the catheter. The fluid seal prevents the reflux of infused fluid from the distal end of the catheter from the bore opening and permits controlled delivery of fluid to affected tissue.

12 Claims, 2 Drawing Sheets

MICROTEXTURED CATHETER AND METHOD FOR PREVENTING CATHETER FLUID REFLUX

BACKGROUND OF THE INVENTION

1. Field of the Invention

This invention relates to catheters for the conduction of fluids to and from internal bodily organs, and more particularly, to a catheter having a surface to be surrounded by living tissue, at least a portion of the surface being microtextured to promote adhesion to and ingrowth of the surrounding tissue. The invention also relates to a method of preventing reflux of fluid supplied to bodily tissue by way of a catheter.

2. Description of the Related Art

Catheters have long found innumerable applications in a wide variety of medical procedures, including both therapeutic and diagnostic procedures. Catheters are eminently useful, for example, as passageways for delivery of fluids to the patient and removal of fluids from the patient. They are thus routinely employed to conduct fluid which contains medicaments from a source thereof directly to the tissue of an internal organ. Such catheters may be placed in the parenchyma of an organ such as the brain or pancreas for direct delivery of medicaments to the parenchyma, usually by way of a bore formed in the tissue of the parenchyma by incision, perforation or puncture.

The body acts spontaneously to reject or encapsulate a foreign body which has been introduced into the body or a specific bodily organ. Such phenomena in connection with implants are described with particularity in U.S. Pat. No. 5,219,361, issued Jun. 15, 1993 to A. F. von Recum et al. In some cases, encapsulation will impede or halt infusion. In others, the delivery fluid will reflux from the tissue through a space opened between the exterior of the catheter and the tissue of the bore in which the catheter is received. Either of these results will greatly diminish the effect of direct infusion of medicaments on affected body tissue. The body's own natural defense systems thus tend to frustrate the procedure.

SUMMARY OF THE INVENTION

The microtextured catheter of the invention and its method of use according to the invention overcome some of the problems of the prior art by attracting and enhancing tissue growth onto a portion of the exterior surface of the catheter, thereby preventing or minimizing the natural responses of the tissue to a foreign body and preventing reflux of the medicament from the bore formed in the tissue in which the catheter is received.

More particularly, a catheter for infusing fluid into a body is provided which comprises a proximal end adapted to be placed in fluid communication with a source of infusate, an opposite distal end to be introduced in a bore formed in living bodily tissue, and at least one fluid discharge aperture. In accordance with the invention, a microtextured external surface portion is formed on the catheter by a plurality of projections and recesses, the relative height and depth of the projections and recesses each being in the range of 1 to 4 microns.

As will be explained with greater particularity hereinbelow, this construction permits the relative direction and containment of infusate supplied to the bore through the catheter to be controlled by the relative location and orientation of the microtextured external surface portion and the fluid discharge aperture and by the ingrowth of bodily tissue into the microtextured external surface portion.

The invention also provides a method for infusing fluid into bodily tissue which comprises the steps of providing such a catheter in fluid communication with a source of infusate, forming a bore in living bodily tissue, inserting the distal end of the catheter into the bore to such an extent that the fluid discharge aperture and the microtextured external surface portion are received in the bore closely adjacent to the bodily tissue, and infusing fluid through the catheter to exit from the fluid discharge aperture and into contact with the bodily tissue forming the catheter bore.

With this method, the bodily tissue immediately adjacent to the microtextured external surface portion of the catheter forms a bond therewith by growing into and intertwining with the microtextured external surface portion.

In one form of this method, the microtextured external surface portion is disposed at a location on the catheter spaced longitudinally inwardly from the distal end thereof and the fluid discharge aperture to form a fluid seal between the microtextured external surface portion and the bodily tissue surrounding the microtextured external surface portion, whereby to form a fluid pocket in the bore surrounding the distal end in communication with the fluid discharge aperture.

In another form of the method, the microtextured external surface portion is located on the catheter at the distal end thereof to extend longitudinally inwardly from the distal end through a predetermined distance, the distal end being inserted in the bore to a depth which at least equals the length of the microtextured external surface portion.

These and other features, objects and advantages of the invention will be apparent from the ensuing description in conjunction with the accompanying drawings.

DETAILED DESCRIPTION OF THE PREFERRED EMBODIMENTS

Figure 1:
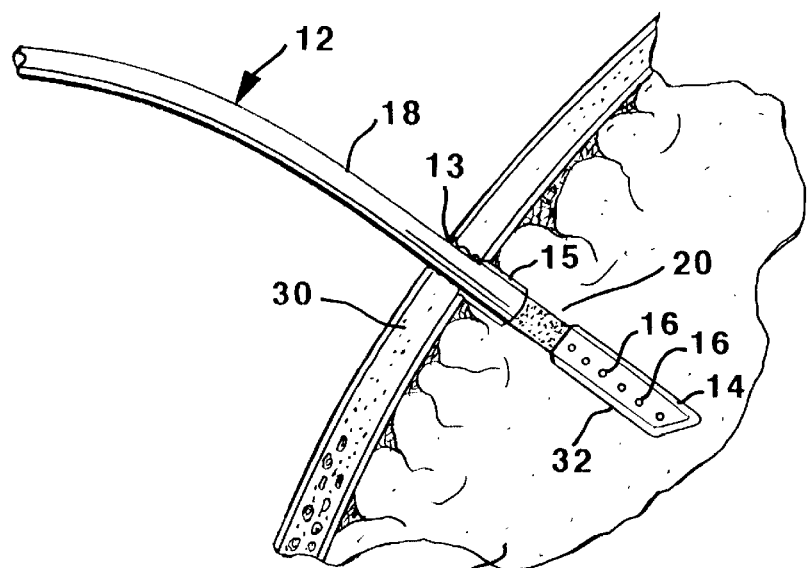
FIG. 1 is a partial view of a catheter according to the invention inserted in a patient's brain, shown partially and in section, for directly infusing medicaments into the parenchyma.
Figure 2:
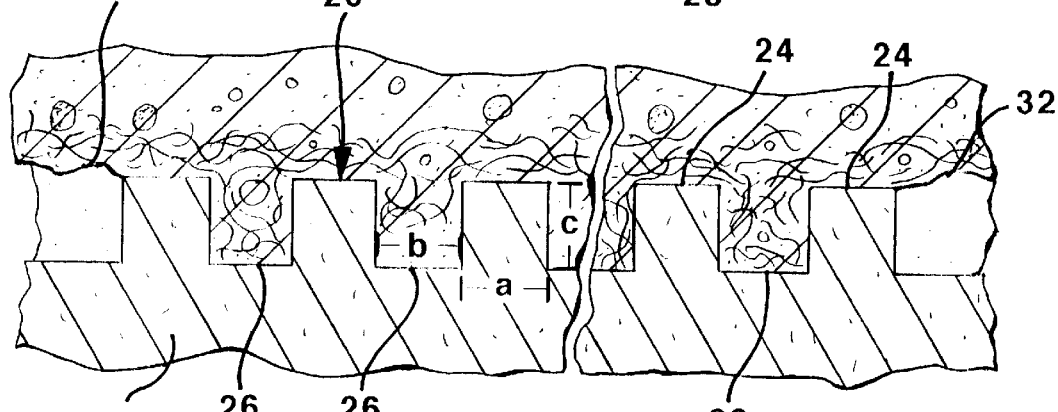
FIG. 2 is a greatly enlarged, fragmentary, diagrammatic representation of a radial section of an exterior, microtextured external surface portion of the catheter of FIG. 1.

Referring now to the drawings and to FIGS. 1 and 2 in particular, a catheter 12 according to the invention comprises a proximal end (not shown) in fluid communication with a source (also not shown) of infusate consisting of a fluid normally containing medicaments, a distal end 14 opposite from the proximal end and provided with a plurality of fluid discharge apertures 16, and a catheter body 18 intermediate the proximal and distal ends. A portion 20 of the exterior surface of the catheter body 18 is textured, while the remaining portions are essentially smooth. More particularly, body portion 20 is microtextured; that is, textured on a microscopic scale, to promote cell and tissue growth into and around the textured surface.

In use, distal end 14 and thus fluid apertures 16 are received in a bore 15 formed in the tissue of the patient. In this instance, the bore is provided in the patient's skull 30 and brain tissue 28 and extends from an opening 13 thereof inwardly to a portion of the parenchyma intended to receive fluid from catheter 12. The microtextured external surface portion 20 of the catheter is disposed along the length thereof at a location such that it will be received inside the patient's body in contact with tissue surrounding bore 15.

As represented diagrammatically in FIG. 2, microtextured external surface portion 20 comprises a repeating pattern of peaks 24 and valleys 26. Peaks 24 and valleys 26 are preferably square in longitudinal or transverse section, or approximately so, whereby the width a of each of the peaks is approximately one micron, the height c of each peak (or the depth of each of the valleys) is approximately one micron, and the width b of each valley is approximately one micron as well. The preferred range for each of these dimensions a, b, c is one to four microns.

While the preferred microtextured structure comprises alternating projections and recesses, any contoured shape having high and low points at intervals of approximately one to four microns is within the scope of the invention. Experimentation has shown that this range results in significant cellular tissue growth into and around the microtextured portion.

Cellular tissue growth to the exterior surface of catheter 12 results in several significant advantages. First, the tissue ingrowth opposes the body's natural reaction of encapsulating a foreign object. Depending upon the relative location of microtextured portion 20 along the length of catheter 12, the tissue ingrowth may act to resist or prevent fluid reflux from distal end 14 of catheter 12 out through bore 15 in the tissue and its opening 13 to the exterior. As seen in FIG. 1, microtextured external surface portion 20 of catheter 12 is bonded to the tissue immediately adjacent to the bore. A bond such as this will block any reflux of fluid by way of bore 15. Therefore, the bore is effectively sealed so that virtually all the medicament flowing through the catheter is received in the parenchyma.

The catheter is formed from a conventional urethane or silicon material such as those commonly used for catheters. The microtexturing formed on catheter 12 may be produced by any one of a variety of conventional processes; for example, by a positive photoresist process, by ion-beam texturing, by plasma etching employing a suitable mask, or by sintering or fusing micro spheres to the exterior surface of the catheter. Alternatively, the surface may be molded into the product by a process described in the aforementioned U.S. Pat. No. 5,219,361 to von Recum et al., which is expressly incorporated herein by reference.

Upon the insertion of a catheter into a properly sized bore in bodily tissue, the body will identify the catheter as a foreign object and will attempt to encapsulate the catheter as a protective reaction. This is commonly known as the foreign body response. Encapsulation would form a relatively impenetrable surface on the exposed tissue of bore 15 so that as fluid was delivered by the catheter, the path of least resistance for subsequent flow would be a passage formed by the surface tissue of bore 15 and the exterior of the catheter, with an exit at bore opening 13. Thus permeation of the affected tissue would be defeated.

The catheter according to the invention is intended to overcome the body's natural tendency to encapsulate by employing microtextured external surface portion 20 to promote tissue ingrowth into and around the catheter. Experimentation has shown that most bodily tissue will actively grow into and bond to such a microtextured external surface. As seen in FIG. 1, microtextured external surface portion 20 is formed intermediate distal end 14 of catheter 12 and bore opening 13. Referring particularly to FIG. 2, the brain tissue 28 immediately adjacent to microtextured external surface portion 20 will grow into, interleave, and intertwine with the peaks and valleys of microtextured external surface portion 20, whereas the brain tissue adjacent to the smooth portions of catheter 12 will attempt to reject or encapsulate their nontextured surfaces. This ingrowth phenomenon causes a fluid pocket 32 to be formed, which extends from microtextured external surface portion 20 of catheter 12 to its distal end 14. Apertures 16 are located in this fluid pocket, and the exterior surface of catheter 12 in the pocket is not textured whereby brain tissue will not bond to it. Similarly, the nontextured portion of catheter body 18 between bore opening 13 and microtextured external surface portion 20 will be encapsulated or rejected by the tissue 28. Adherence of tissue to the microtextured portion of the catheter can be enhanced by using a polymer with a surface modified to be hydrophilic. This hydrophilic surface can be accomplished by either coating the surface with a hydrophilic coating or by using a hydrophilic polymer in the desired area. In this embodiment, the nontextured portion of the catheter should preferably have a hydrophobic surface.

The formation of fluid pocket 32 provides significant advantages for the retention of infused fluids by the affected tissue. In particular, the ingrowth of cellular brain tissue into microtextured external surface portion 20 effectively seals bore 15 so that fluid flowing delivered from apertures 16 into fluid pocket 32 cannot escape or reflux out from bore opening 13 but is instead forced to permeate the tissue 28. Because reflux of fluid passing through the catheter may thus be prevented, the catheter according to the invention may be used effectively for the delivery of a wide variety of fluids, including, but not limited to, medications, growth factors, antisense agents, ionic solutions, antibodies, hormones, proteins, peptides, viruses, cell suspensions, chemotherapeutic agents, toxins, or any suitable combination thereof. The listing of infusion agents described above is intended to be an illustrative listing and by no means an exhaustive identification of suitable substances to be delivered by the catheter according to the invention.

Figure 3:
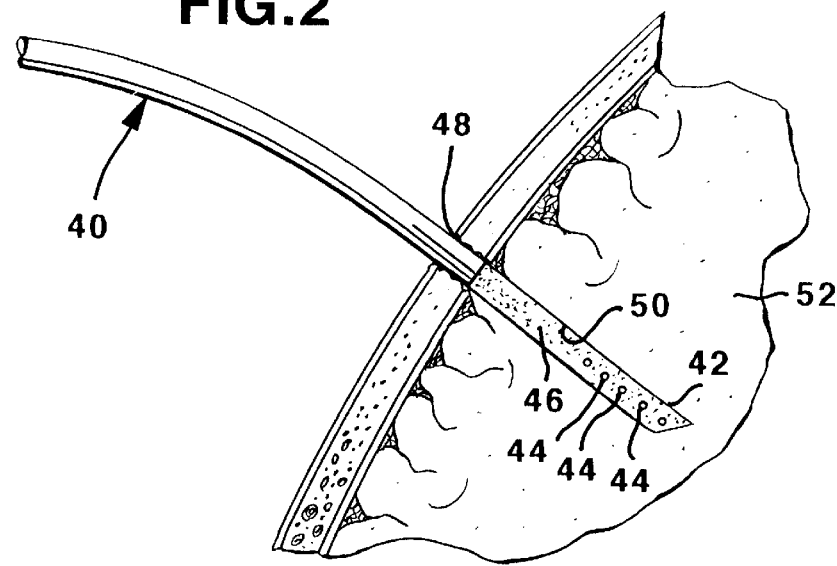
FIG. 3 is a view similar to FIG. 1, but showing an alternative embodiment of the catheter according to the invention.
Figure 4:
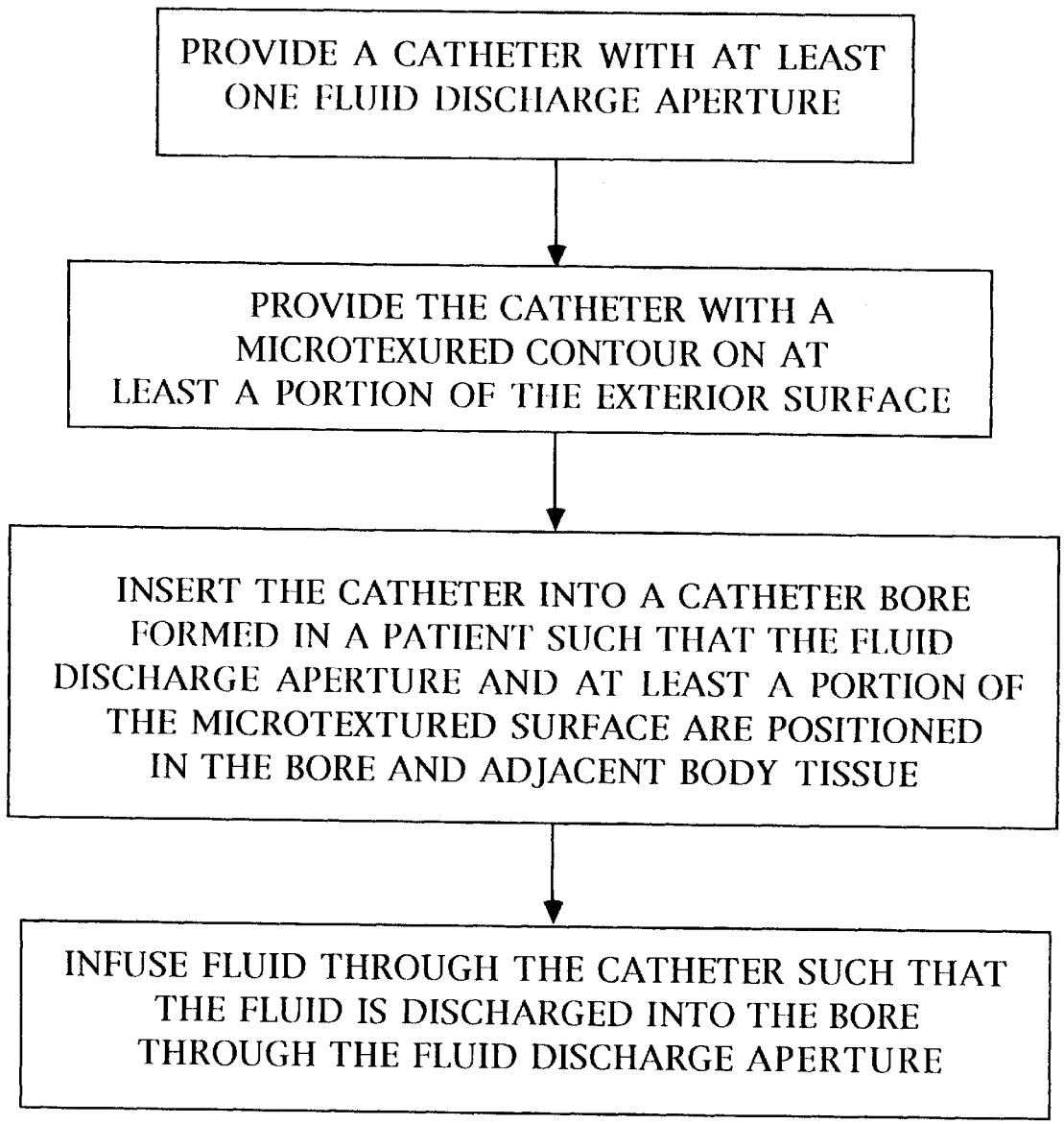
FIG. 4 is a schematic flow diagram of the method according to the invention for preventing fluid reflux with a catheter having a microtextured external surface portion.

FIG. 3 shows an alternative embodiment of a catheter according to the invention. In this embodiment, a catheter 40 has a distal end 42, a proximal end (not shown), and a plurality of apertures 44 formed along a length of the catheter adjacent to distal end 42. Catheter 40 passes through a bore opening 48 formed in the skull of a patient and is received in a bore 50 formed in brain tissue 52. In this embodiment, a microtextured portion 46 of catheter 40 extends along that entire length of the catheter that is received in the brain tissue 52. Therefore, the brain tissue will bond to substantially the entire length of the catheter inside bore 50. As fluid is infused through the catheter, the fluid will be directed to the tissue immediately adjacent to each of apertures 44.

As is apparent, the placement and extent of microtexturing on the exterior surface of the catheter affords the surgeon significant control and flexibility in the delivery and direction of fluid flow from the catheter. The placement, arrangement, and orientation of the apertures of catheter 40 may be coordinated with the extent of and location of the microtextured portion or portions of the exterior surface of the catheter. For example, all of the apertures might be clustered along one side of the catheter with the microtextured external surface portion spaced axially or radially from the apertures, thereby to control the direction of fluid flow. Alternatively, the apertures might be staggered over a relatively long distance, so that a large area of tissue would be exposed directly to the infused fluid, and this in combination with microtextured bands spaced along the length of the catheter to create multiple pockets.

The microtextured catheter according to the invention is ideally suited for use with an implantable pump for the direct delivery of fluid to the brain parenchyma. The catheter may be used with a conventional pump, such as the SynchroMed™ pump commercially available from Medtronic, Inc. of Minneapolis, Minn. This pump delivers fluids directly to the brain parenchyma through a catheter at flow rates of onehalf microliter per hour to three microliters per minute.

Though the preferred embodiments are shown as directing fluids to the brain parenchyma, the microtextured catheter according to the invention may be utilized with virtually any human organ having tissue which exhibits a tendency to grow into the microtextured external surface. In the end, the microtextured catheter according to the invention is limited only by the creativity of the user in positioning the fluid apertures and microtextured external surface along the length of the catheter.

While the invention has been particularly described in connection with certain specific embodiments thereof, it is to be understood that this is by way of illustration and not of limitation, and the scope of the appended claims should be construed as broadly as the prior art will permit.

What is claimed is:

1. A method for preventing reflux along the exterior surface of a catheter of a fluid infused into bodily tissue through the catheter, the method comprising the steps of:

providing a catheter in fluid communication with a source of infusate, the catheter having a distal end, at least one fluid discharge aperture at the distal end, and a microtextured exterior surface portion formed of a plurality of alternating projections and recesses, the height and depth of said projections and recesses each being in the range of 1 to 4 microns, the microtextured exterior surface portion being located proximal to the at least one fluid discharge aperture;

forming a bore in living bodily tissue;

inserting the distal end of the catheter into the bore to such an extent that the fluid discharge aperture and the microtextured external surface portion are received in the bore closely adjacent to the bodily tissue;

infusing fluid through the catheter to exit the catheter from the fluid discharge aperture and into contact with the bodily tissue forming the catheter bore;

whereby the bodily tissue immediately adjacent to the microtextured external surface portion of the catheter exterior surface forms a bond therewith by growing into and intertwining with the microtextured external surface portion thereby forming a seal to prevent the reflux of fluid exiting the catheter through the fluid discharge opening past the seal.

2. A method according to claim 1, wherein the step of providing a catheter includes the step of providing the microtextured external surface portion on the catheter at the distal end thereof to extend longitudinally inwardly from the distal end through a predetermined distance at least equal to the depth of the bore where the distal end is to be introduced.

3. A method according to claim 1, wherein the step of providing a catheter includes the step of providing a hydrophilic microtextured external surface portion.

4. A method according to claim 1, wherein the step of providing a catheter includes the step of coating the microtextured external surface with a hydrophilic coating.

5. A method according to claim 1, wherein the step of providing a catheter includes the step of providing the external surface of the catheter that is not part of the microtextured external surface portion with a hydrophobic surface.

6. A method according to claim 5, wherein the step of providing a catheter includes the step of providing the microtextured external surface made of a hydrophilic polymer.

7. A method for preventing reflux along the exterior surface of a catheter of a fluid infused into bodily tissue through the catheter, the method comprising the steps of:

providing a catheter in fluid communication with a source of infusate, the catheter having a distal end, at least one fluid discharge aperture at the distal end, and a microtextured exterior surface portion formed of a plurality of alternating projections and recesses, the height and depth of said projections and recesses each being in the range of 1 to 4 microns, the microtextured exterior surface being located around the at least one fluid discharge aperture;

forming a bore in living bodily tissue;

inserting the distal end of the catheter into the bore to such an extent that the fluid discharge aperture and the microtextured external surface portion are received in the bore closely adjacent to the bodily tissue;

infusing fluid through the catheter to exit the catheter from the fluid discharge aperture and into contact with the bodily tissue forming the catheter bore;

whereby the bodily tissue immediately adjacent to the microtextured external surface portion of the catheter exterior surface forms a bond therewith by growing into and intertwining with the microtextured external surface portion thereby forming a seal to prevent the reflux of fluid exiting the catheter through the fluid discharge opening past the seal.

8. A method according to claim 7, wherein the step of providing a catheter includes the step of providing the microtextured external surface portion on the catheter at the distal end thereof to extend longitudinally inwardly from the distal end through a predetermined distance at least equal to the depth of the bore where the distal end is to be introduced.

9. A method according to claim 7, wherein the step of providing a catheter includes the step of providing a hydrophilic microtextured external surface portion.

10. A method according to claim 7, wherein the step of providing a catheter includes the step of coating the microtextured external surface with a hydrophilic coating.

11. A method according to claim 7, wherein the step of providing a catheter includes the step of providing the external surface of the catheter that is not part of the microtextured external surface portion with a hydrophobic surface.

12. A method according to claim 11, wherein the step of providing a catheter includes the step of providing the microtextured external surface made of a hydrophilic polymer.

* * * * *